United States Patent [19]
Yoon

[11] Patent Number: 5,573,540
[45] Date of Patent: Nov. 12, 1996

[54] APPARATUS AND METHOD FOR SUTURING AN OPENING IN ANATOMICAL TISSUE

[76] Inventor: InBae Yoon, 2101 Highland Ridge Dr., Phoenix, Md. 21131

[21] Appl. No.: 276,670

[22] Filed: Jul. 18, 1994

[51] Int. Cl.⁶ .................................................. A61B 17/04
[52] U.S. Cl. ........................... 606/139; 606/144; 606/148
[58] Field of Search ...................... 606/139, 144, 606/146, 148, 145, 147; 112/163, 169

[56] References Cited

U.S. PATENT DOCUMENTS

| | | | |
|---|---|---|---|
| 4,553,543 | 11/1985 | Amarasinghe | 606/148 |
| 5,021,059 | 6/1991 | Kensey et al. | 606/213 |
| 5,222,508 | 6/1993 | Contarini | 606/139 |
| 5,304,184 | 4/1994 | Hathaway et al. | 606/148 |
| 5,320,632 | 6/1994 | Heidmueller . | |
| 5,350,385 | 9/1994 | Christy | 606/146 |
| 5,364,408 | 11/1994 | Gordon . | |
| 5,368,601 | 11/1994 | Sauer et al. | 606/144 |
| 5,374,275 | 12/1994 | Bradley et al. | 606/144 |
| 5,391,182 | 2/1995 | Chin | 606/144 |
| 5,403,329 | 4/1995 | Hinchcliffe . | |
| 5,417,699 | 5/1995 | Klein et al. | 606/144 |
| 5,439,469 | 8/1995 | Heaven et al. | 606/144 |
| 5,462,561 | 10/1995 | Voda | 606/144 |
| 5,470,338 | 11/1995 | Whitfield et al. | 606/144 |
| 5,476,469 | 12/1995 | Hathaway et al. | 606/144 |

*Primary Examiner*—Gary Jackson

[57] ABSTRACT

An apparatus for suturing an opening in anatomical tissue includes at least one length of suture material, a leg support terminating distally in at least two hooks having sharp tips for threading the length of suture material through anatomical tissue adjacent an opening, and an operating mechanism coupled with the leg support for advancing and retracting the hooks. The apparatus further includes a housing, such as a stabilizer or a cannula, defining a portal through the opening for passage of the hooks. Each hook is carried by a single leg supported by a hub or secured along its length to other legs to form a handle for operating the hooks. If the legs are carried by a hub, the hub is movable relative to the housing to advance and retract the hooks within passages formed in the housing. The legs can be hollow or slotted to allow passage of the lengths of suture material through the legs or each length of suture material can be attached near the distal end of one of the sharp tissue penetrating tips and pulled through the tissue. The tissue adjacent the opening is drawn together via the lengths of suture material passed through the tissue by advancing the lengths through the hollow legs or by being pulled along with the sharp tissue penetrating tips of the hooks.

29 Claims, 8 Drawing Sheets

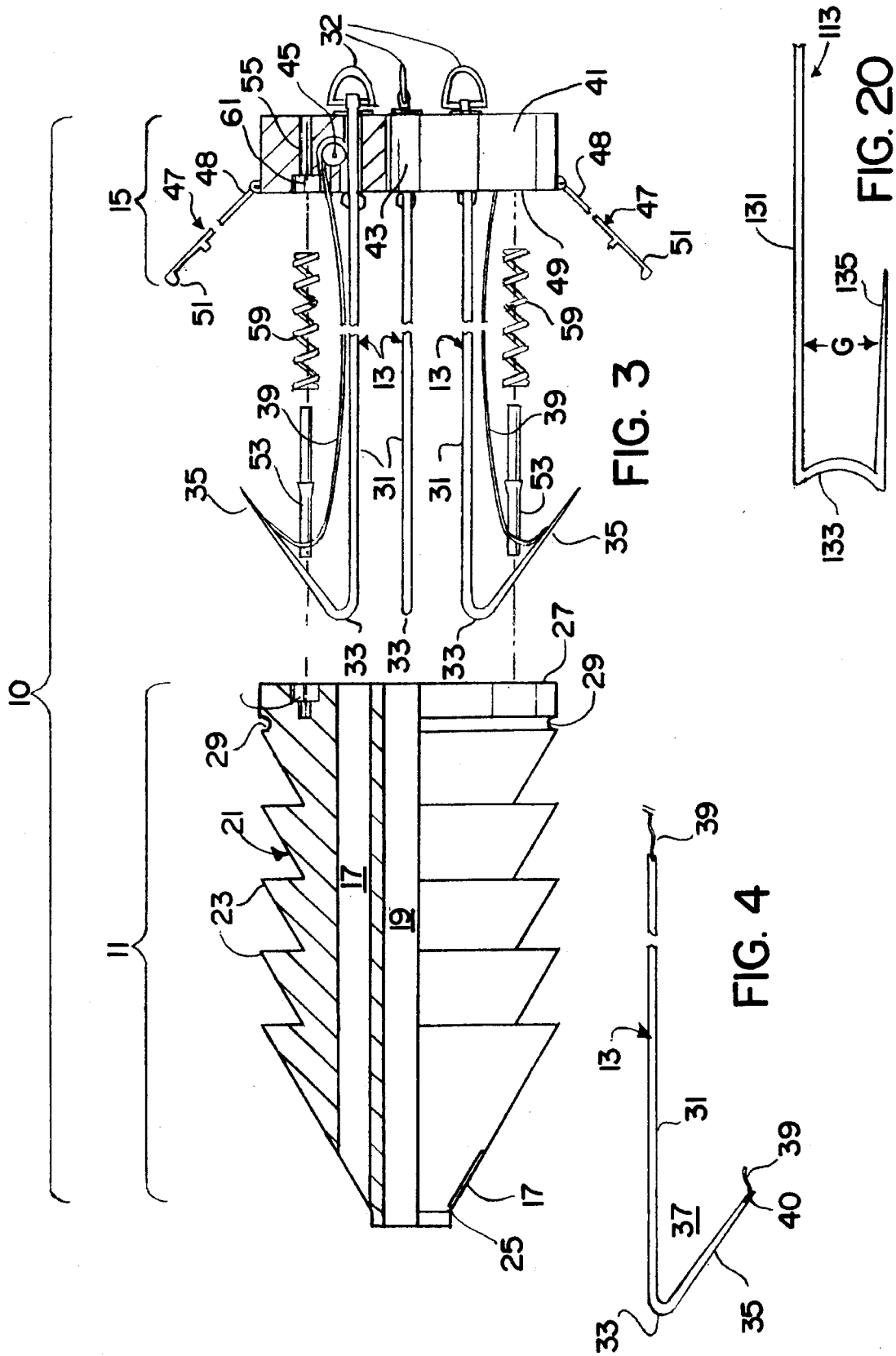

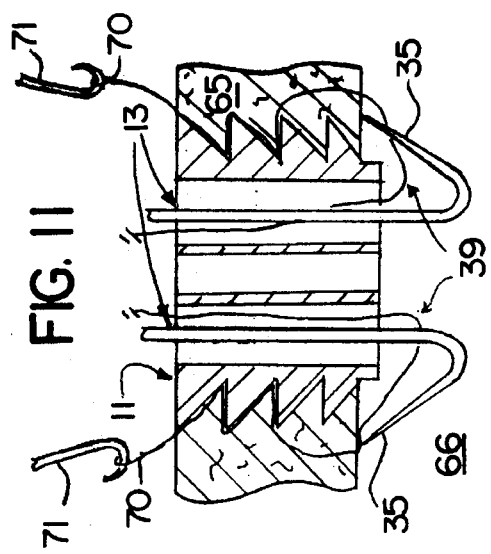
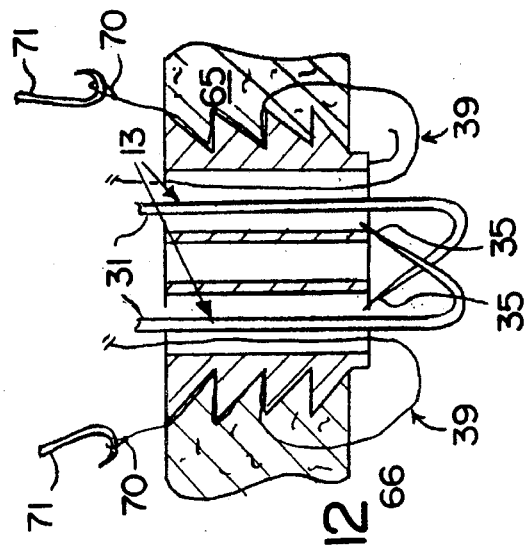
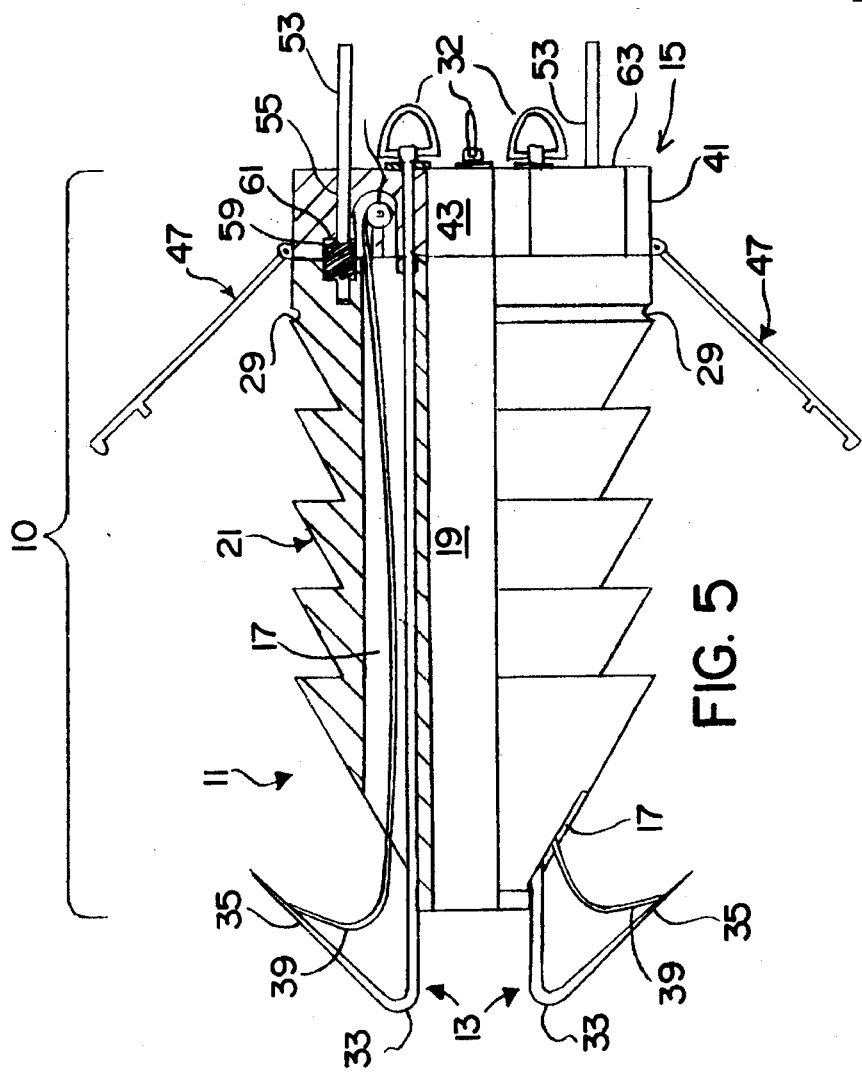

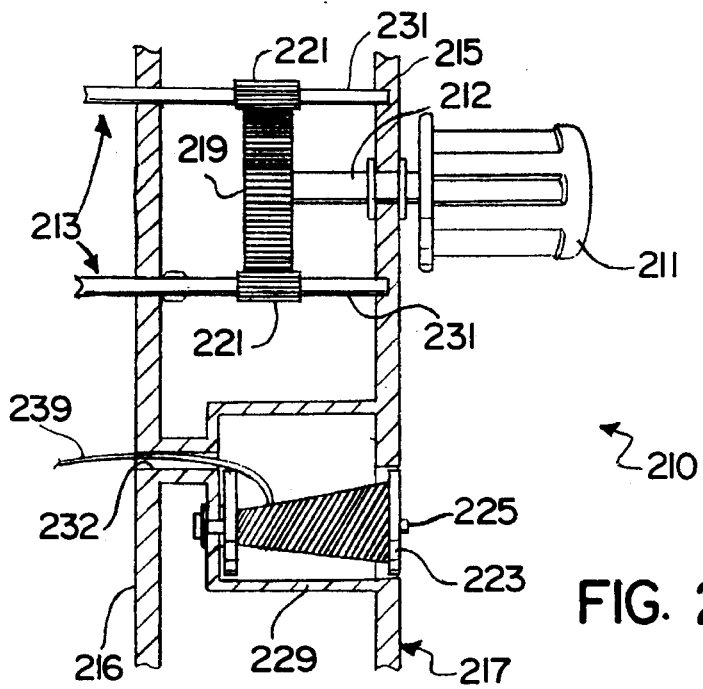
FIG. 23
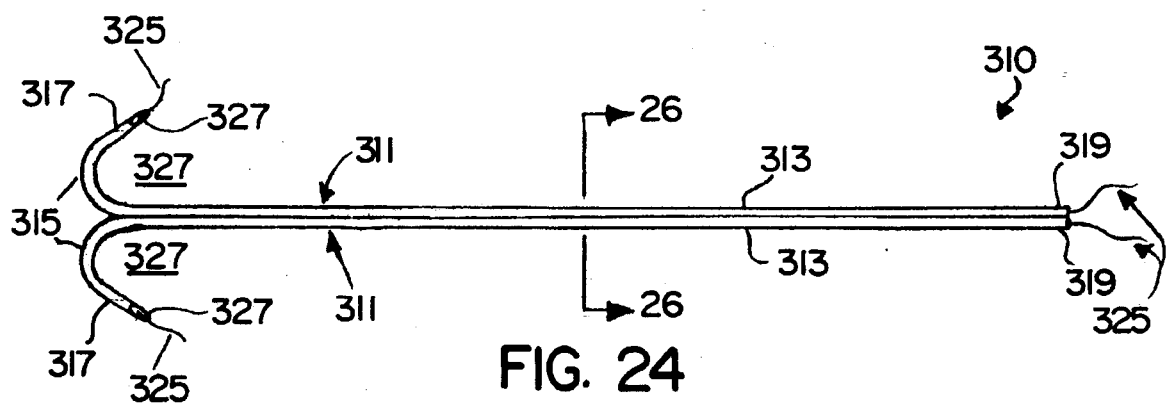
FIG. 24
FIG. 25
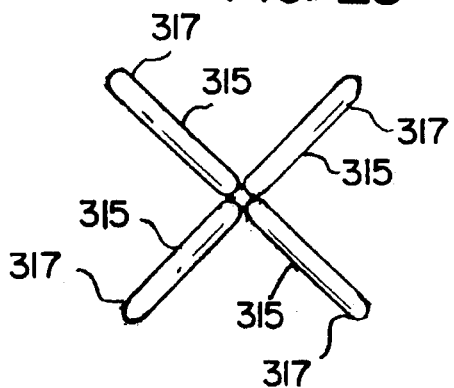
FIG. 26
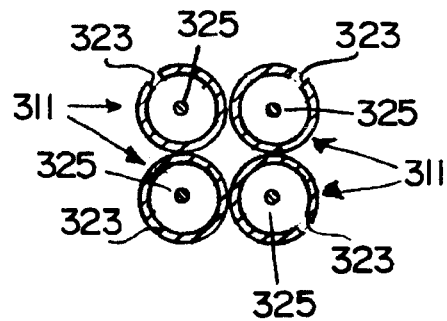

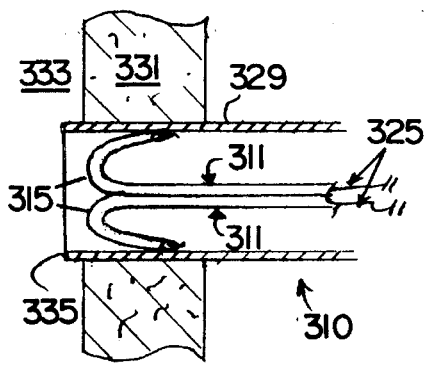
FIG. 27
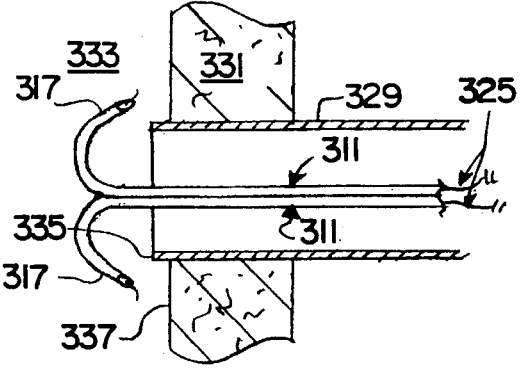
FIG. 28
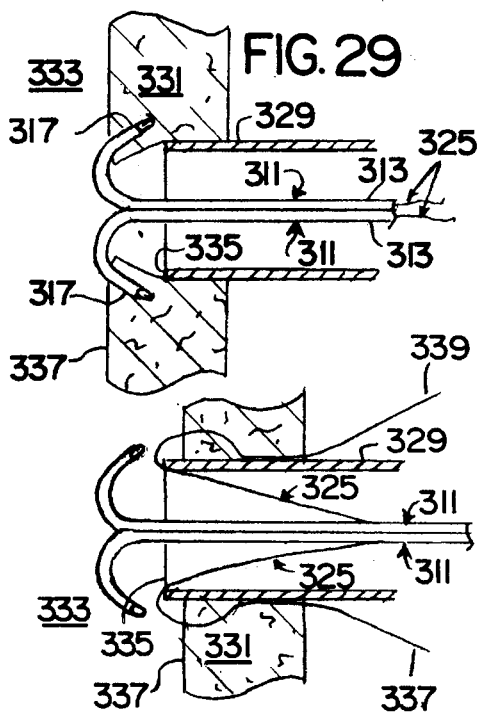
FIG. 29
FIG. 31
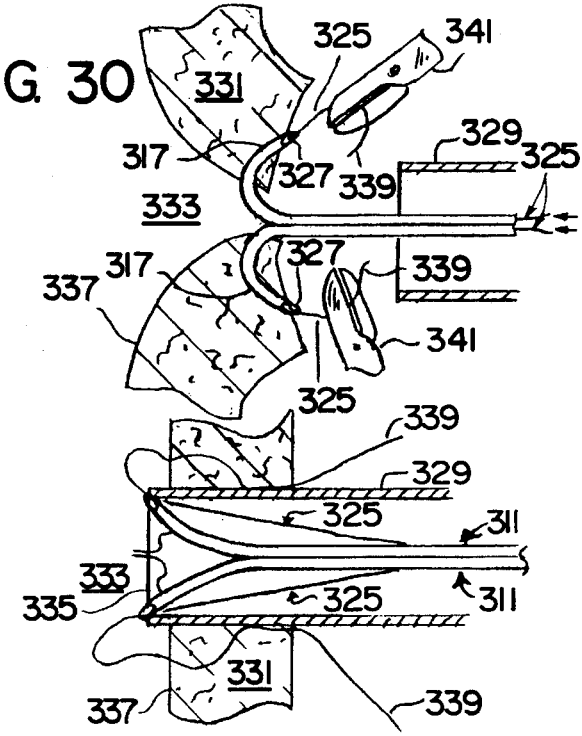
FIG. 30
FIG. 32
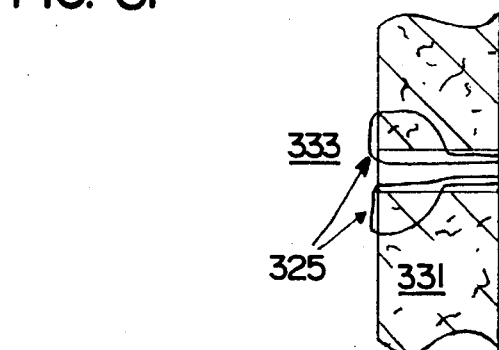
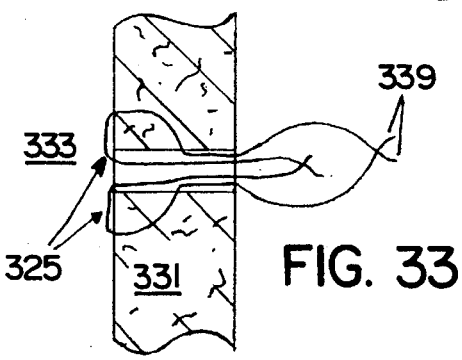
FIG. 33

APPARATUS AND METHOD FOR SUTURING AN OPENING IN ANATOMICAL TISSUE

BACKGROUND OF THE INVENTION

1. Field of the Invention

The present invention relates generally to surgical instruments and procedures and, more particularly, to an apparatus and method for suturing an opening in anatomical tissue, such as a puncture site created for introduction of instruments during endoscopic and other minimally invasive procedures.

2. Description of the Background Art

Endoscopic and minimally invasive medical procedures, such as laparoscopy, have become widely accepted for surgery and diagnosis due to the associated advantages relating to reduced trauma and hospitalization time. The performance of an endoscopic procedure, however, requires the creation of one or more puncture sites through a wall of an anatomical cavity to permit introduction of instruments such as portal sleeves or cannulas, endoscopes, ligating appliers, forceps, cauteries and the like into the anatomical cavity. The puncture sites are normally created by means of a penetrating instrument including an obturator, such as a trocar, disposed within a portal sleeve such that, after the penetrating instrument has penetrated into the anatomical cavity, the obturators are withdrawn leaving the sleeves in place to form portals in the cavity wall. Once the endoscopic procedure has been completed, the sleeves are withdrawn and the puncture sites are closed.

Herniation through an improperly closed puncture site in the wall of an anatomical cavity is one of the rare postoperative complications associated with endoscopic procedures that can lead to significant morbidity. With the increased use of endoscopic procedures and the use of larger endoscopic portals an increase in the incidence of such complications can be expected. Even where a defect is small, there is still the possibility of small bowel entrapment in a Richter's type hernia at the site of introduction of the trocar or other penetrating instrument. Hence, it is important that the puncture site be closed or approximated following removal of the endoscopic instruments.

While complications such as herniation and small bowel entrapments can be avoided by suture of the puncture site in the cavity wall, this involves a time consuming and trauma causing procedure whereby the defect in the cavity wall is enlarged and manipulated to provide access for performing suturing of the interior layers, such as the fascia, using standard curved suturing needles and lengths of suture material. Additionally, in other medical procedures, such as anastomosis, bladder reattachment and repair of congenital or noncongenital defects in the wall of an anatomical cavity such as the abdomen, bowel, small blood vessels such as veins and arteries, epidural, plural and subarachnoid spaces, heart ventricles and spinal and synovial cavities, it is important to quickly and securely repair the opening or separation in the anatomical tissue. In minimally invasive procedures in particular, suturing of the anatomical tissue is both time consuming and difficult as the suture needles and lengths of suture material must be grasped using instruments manipulated remotely from the operative site through narrow cannulas or sleeves.

SUMMARY OF THE INVENTION

Accordingly, it is a primary object of the present invention to overcome the above mentioned disadvantages of the prior art and to provide an apparatus for suturing an opening in anatomical tissue with a plurality of hooks for passing one or more lengths of suture material through the anatomical tissue adjacent the opening so that the lengths can be grasped externally of the opening and drawn together to suture the opening.

Another object of the present invention is to pass the hooks of an apparatus for suturing an opening in anatomical tissue through a housing inserted into the opening to penetrate a distal surface of the anatomical tissue with sharp tissue penetrating tips of the hooks to pass lengths of suture material through distal layers of the tissue.

A further object of the present invention is to resiliently deform at least a distal portion of the hooks of an apparatus for suturing an opening in anatomical tissue within a housing inserted into the opening to cause the sharp tissue penetrating tips of the hooks to spring radially outward upon emerging from a distal end of the housing to face a distal surface of the anatomical tissue adjacent the opening.

Yet another object of the present invention is to rotatably carry the hooks of an apparatus for suturing an opening in anatomical tissue on a hub for rotation from a folded position within the housing to a radially extending position wherein the sharp tissue penetrating tips of the hooks face a distal surface of the anatomical tissue adjacent the opening.

An additional object of the present invention is to utilize hollow hooks in an apparatus for suturing an opening in anatomical tissue to advance lengths of suture material through the anatomical tissue.

Still another object of the present invention is to attach lengths of suture material adjacent the sharp tissue penetrating tips of a plurality of hooks in an apparatus for suturing an opening in anatomical tissue.

Yet a further object of the present invention is to utilize a stabilizer as a housing to form one or more passages through which a plurality of hooks are moved to access a distal surface of anatomical tissue surrounding the housing and to pass lengths of suture material through the tissue to suture an opening bounded by the tissue.

The present invention has another object in that a distal surface of anatomical tissue adjacent an opening is penetrated using proximal-facing tips of at least two outwardly turned hooks and is inverted so that the tips pierce through the tissue allowing lengths of suture material to be passed through the tissue and grasped on a proximal side of the tissue to suture the opening.

Some of the advantages of the present invention over the prior art are that the apparatus can penetrate distal surfaces of anatomical tissue adjacent an opening to pass lengths of suture material through the tissue to suture the opening without expansion, enlargement or extension of the opening, that the apparatus can be operated through narrow passages formed in a stabilizer or through a portal sleeve such as are commonly positioned for use during minimally invasive procedures, and that familiar suturing techniques can be used for approximating the opening once the apparatus has been used to pass lengths of suture material through the tissue adjacent the opening.

The present invention is generally characterized in an apparatus for suturing an opening in anatomical tissue including at least one length of suture material, leg means terminating distally in at least two hooks having sharp tissue penetrating tips for passing the length of suture material through anatomical tissue adjacent the opening, and an operating mechanism coupled with the leg support for advancing and retracting the hooks. The apparatus further includes a housing, such as a stabilizer or a cannula, defining a portal through the opening for passage of the hooks. Each hook is carried by a single leg supported by a hub or secured along its length to other legs to form a handle for operating the hooks. The hub is movable relative to the housing to advance and retract the hooks within passages formed in the housing. The legs can be hollow or slotted to allow passage of the lengths of suture material through the legs or each length of suture material can be attached near the distal end of one of the sharp tissue penetrating tips and pulled through the tissue.

Another aspect of the present invention is generally characterized in a method of suturing an opening in anatomical tissue including the steps of penetrating anatomical tissue adjacent the opening with proximal-facing tips of at least two outwardly turned hooks, pulling the hooks in a proximal direction to invert the tissue adjacent the opening, piercing through the inverted tissue to expose the proximal facing tips, using the hooks to pass lengths of suture material through the anatomical tissue and grasping distal ends of the lengths of suture material. The tissue adjacent the opening is drawn together via the lengths of suture material passed through the tissue by advancing the lengths through hollow legs of the hooks or by being pulled along with the sharp tissue penetrating tips of the hooks.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 3 is an exploded side view, partly in section, of the apparatus of FIG. 1.

FIG. 4 is a side view of a hollow hook for use in the apparatus of FIG. 1.

FIG. 5 is a side view, partly in section, of the apparatus of FIG. 1 with hooks deployed.

FIGS. 7–16 are broken views, partly in section, illustrating use of the apparatus of the present invention for closing a puncture site in the wall of an anatomical cavity.

FIG. 20 is a frontal view of the apparatus of FIG. 19.

FIG. 23 is a broken view, partly in section, of a modified hub according to the present invention for concurrently turning multiple hooks.

FIG. 24 is a side view of another modification of the apparatus of the present invention.

FIG. 25 is a frontal view of the apparatus of FIG. 24.

FIG. 26 is a cross-sectional view taken along line 26—26 in FIG. 24.

FIGS. 27–33 are broken views, partly in section, illustrating use of the apparatus of FIG. 24.

DETAILED DESCRIPTION OF THE PREFERRED EMBODIMENTS

The apparatus and method of the present invention can be utilized to suture closed any type of opening in biological tissue; and, accordingly, while the apparatus and method are described hereinafter for use in closing a puncture site opening after endoscopic procedures, such as laparoscopy, the apparatus can be used to perform anastomosis, reconstructive surgery such as bladder reattachment or to repair a hernia or ruptured bowel or any other congenital or non-congenital separation between tissue segments or openings in a wall of an anatomical cavity, such as the abdomen, small blood vessels such as veins and arteries, epidural, plural and subarachnoid spaces, heart ventricles and spinal and synovial cavities.

Figure 2:
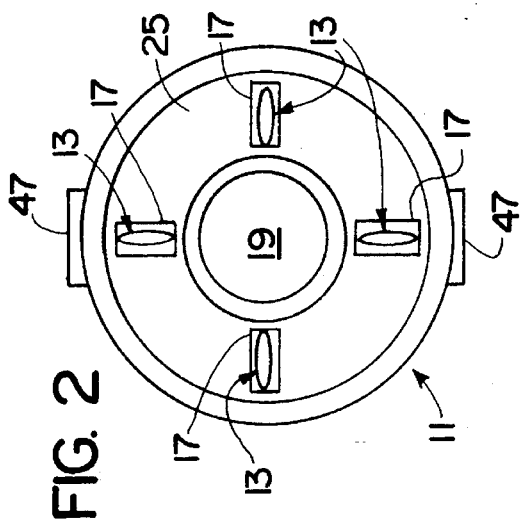
FIG. 2 is a frontal view of the apparatus of FIG. 1.
Figure 1:
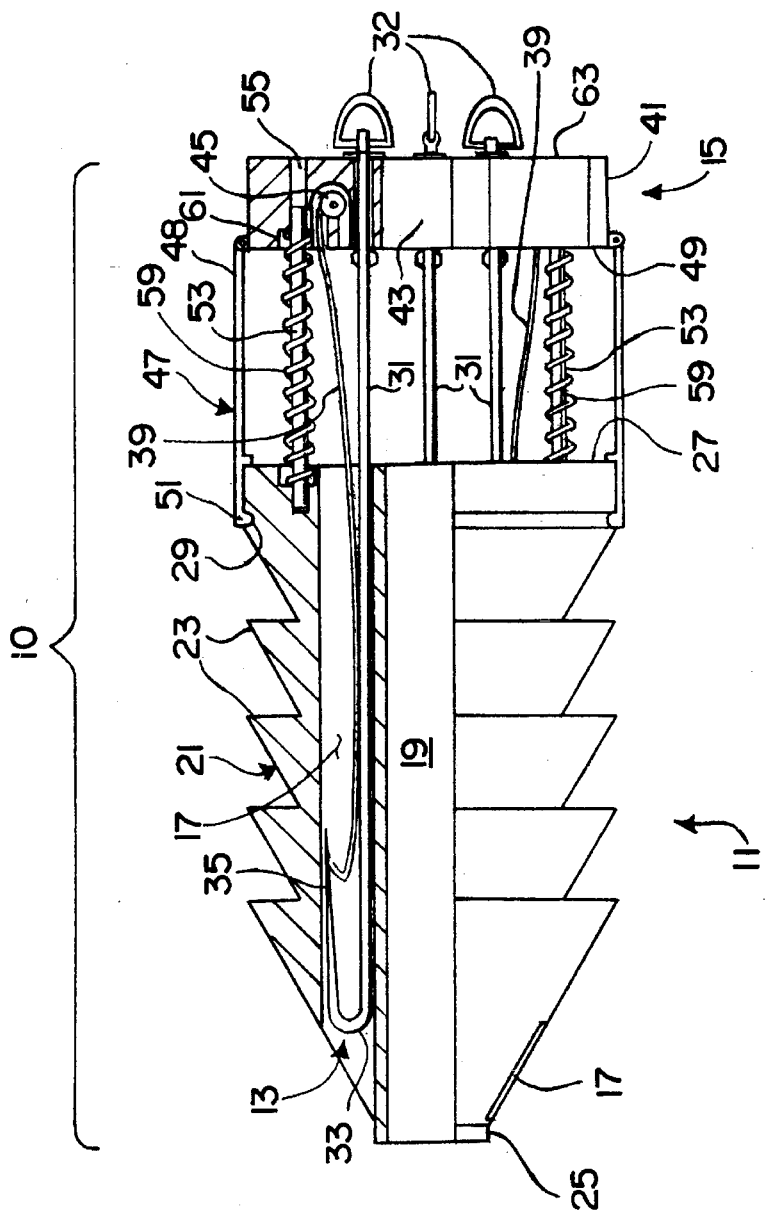
FIG. 1 is a side view, partly in section, of an apparatus for suturing an opening in anatomical tissue according to the present invention.

A puncture site closure apparatus 10 according to the present invention, shown in FIGS. 1–3, includes a tissue engaging stabilizer 11, one or more hooks 13, and a hub 15 for providing means to support and displace the hooks 13 through annularly spaced passages 17 formed through the stabilizer 11. The stabilizer 11 is a generally tubular member defining a central lumen 19 for receiving elongate instruments such as a cannula or portal sleeve and a tissue engaging exterior plug surface 21 having one or more ridges or ribs 23. The distal end 25 of the stabilizer 11 is generally frustoconical in shape to ease insertion through a puncture site or other opening in the wall of an anatomical cavity. The stabilizer 11 has a generally cylindrical proximal end 27 and an annular groove 29 formed on an exterior circumferential surface spaced distally from the proximal end 27. The annularly spaced passages 17 are defined longitudinally within the tubular wall of the stabilizer 11 between the central lumen 19 and tissue engaging surface 21 to provide an opening between the distal and proximal ends 25 and 27 of the stabilizer 11. As best seen in FIG. 2, the passages 17 resemble narrow radial slits equally angularly spaced around the central lumen 19 when viewed from the distal end 25 of the stabilizer 11.

One or more hooks 13 are housed within the passages 17 defined in the stabilizer 11; four hooks 13 being shown, and each hook 13 including an elongate leg 31 having an acutely bent distal portion 33 terminating in a sharp tissue penetrating tip 35. As shown in FIG. 3, the sharp tissue penetrating tip 35 of each hook 13 is normally angled back toward the proximal end of the leg 31 at a diverging angle to define a tissue receiving space 37 of diminishing width in a distal direction with the distance between the sharp tissue penetrating tip 35 and leg 31 being normally greater than the radial height of each passage 17. All or a portion of each hook 13 can be formed of a medically-acceptable resilient or semirigid material so as to be deformable to fit within the passages 17 as shown in FIG. 1 and can be bioabsorbable or non-bioabsorbable and hollow, as shown in FIG. 4, or slotted to provide a passage way for lengths of suture material 39 such that the lengths run through the leg 31 of each hook 13 and exit through an opening 40 at or near the tip 35, or lengths of suture material 39 can be attached near the sharp tissue penetrating tip 35 of each leg 31 as shown in FIG. 3.

The proximal end of each leg 31 is rotatably carried by the hub 15 and coupled with a knob 32 lockable in one or more positions for controlling rotation of the leg 31. The hub 15 includes a generally cylindrical body 41 longitudinally spaced from the proximal end 27 of the stabilizer 11 and defines a central bore 43 for passage of a cannula or other elongate member. One or more spools 45 are carried by the cylindrical body 41 for supplying lengths of suture material 39 to the hooks 13 and a pair of diametrically opposed latching arms 47 are hinged at proximal ends 48 to the body 41 near a distal face 49 of the body 41 with distal ends 51 of each arm 47 being configured to meet with the annular groove 29 formed near the proximal end 27 of the stabilizer 11.

The puncture site closure apparatus 10 is assembled prior to use as shown in FIG. 1 so that, in the assembled condition, the hub 15 is axially aligned with a longitudinal axis of the stabilizer 11 and spaced a predetermined distance from the proximal end 27 of the stabilizer 11. The cylindrical body 41 of the hub 15 is maintained at the predetermined distance by the hinged latches 47 which extend distally from the cylindrical body 41 and engage the annular groove 29 or some other physical feature of the stabilizer 11 to lock the hub 15 in place relative to the stabilizer 11. Cylindrical guide pins 53 extend between the cylindrical body 41 of the hub 15 and a proximal end 27 of the stabilizer 11, and are received proximally in circular through-holes 55 formed inside the periphery of the cylindrical body 41. A distal end of each guide pin 53 is received in a blind hole 57 formed in the stabilizer 11 and aligned with the through-hole 55 in the cylindrical body 41 of the hub 15. A spring 59 circumscribes each guide pin 53 and is held in compression between the proximal end 27 of the stabilizer 11 and the distal face 49 of the hub 15. Through-holes 55 formed in the cylindrical body 41 of the hub 15 terminate near the distal face 49 of the hub 5 in an increased diameter spring recess 61.

The predetermined distance separating the distal face 49 of the cylindrical hub 15 and the proximal end 27 of the stabilizer 11 is chosen to at once maintain the sharp tissue penetrating tips 35 of the hooks 13 completely within the passages 17 formed in the stabilizer 11 and to provide the degree of travel necessary for displacement of the sharp tissue penetrating tips 35 of the hooks 3 through open distal ends of the passages 17. With cylindrical hub 15 locked in the position shown in FIG. 1, however, the sharp tissue penetrating tips 35 of the hooks 13 are completely disposed within the passages 17 of the stabilizer 11, and it is therefore possible to grasp the stabilizer 11 so that it can be inserted into the wall of an anatomical cavity, for example, without inadvertently exposing the sharp tissue penetrating tips 35 of the hooks 13.

Hooks 13 are movable from their retracted position within the stabilizer 11 to a deployed position illustrated in FIG. 5, to expose the sharp tissue penetrating tip 35 of each hook 13. In order to move the hooks 13, the cylindrical hub 15 is moved distally toward the proximal end 27 of the stabilizer 11 until the sharp tissue penetrating tips 35 of the hooks 13 are deployed as shown or the distal face 49 of the cylindrical hub 15 abuts the proximal end 27 of the stabilizer 11. Displacement of the cylindrical hub 15 in a distal direction also causes the guide pins 53 to pass through the holes 55 to ultimately protrude from the proximal face 63 of the cylindrical hub 15 and to compress the springs 59 within spring recesses 61 defined in the distal face 49 of the cylindrical hub 15. In FIG. 5, the hinged latches 47 are shown detached from the annular groove 29 and rotated away from the stabilizer 11 so as to avoid obstructing the movement of the cylindrical hub 15 toward the stabilizer 11. With cylindrical hub 15 positioned proximal the stabilizer 11, the hooks 13 protrude from an open distal end of each passage 17 so that the sharp penetrating tips 35 of the hooks 13 extend proximally and radially outward. Since each hook 13 was elastically restrained within a passage 17 when retracted within the stabilizer 11, the hooks 13 spring radially outward upon exiting the open distal ends of the passages 17. The length and angular divergence of the tissue penetrating tips 35 of each hook 13 are chosen such that in an exposed condition, the tip 35 of each hook 13 extends radially beyond an outer periphery of the exterior tissue engaging surface 21 of the stabilizer 11.

Figure 6:
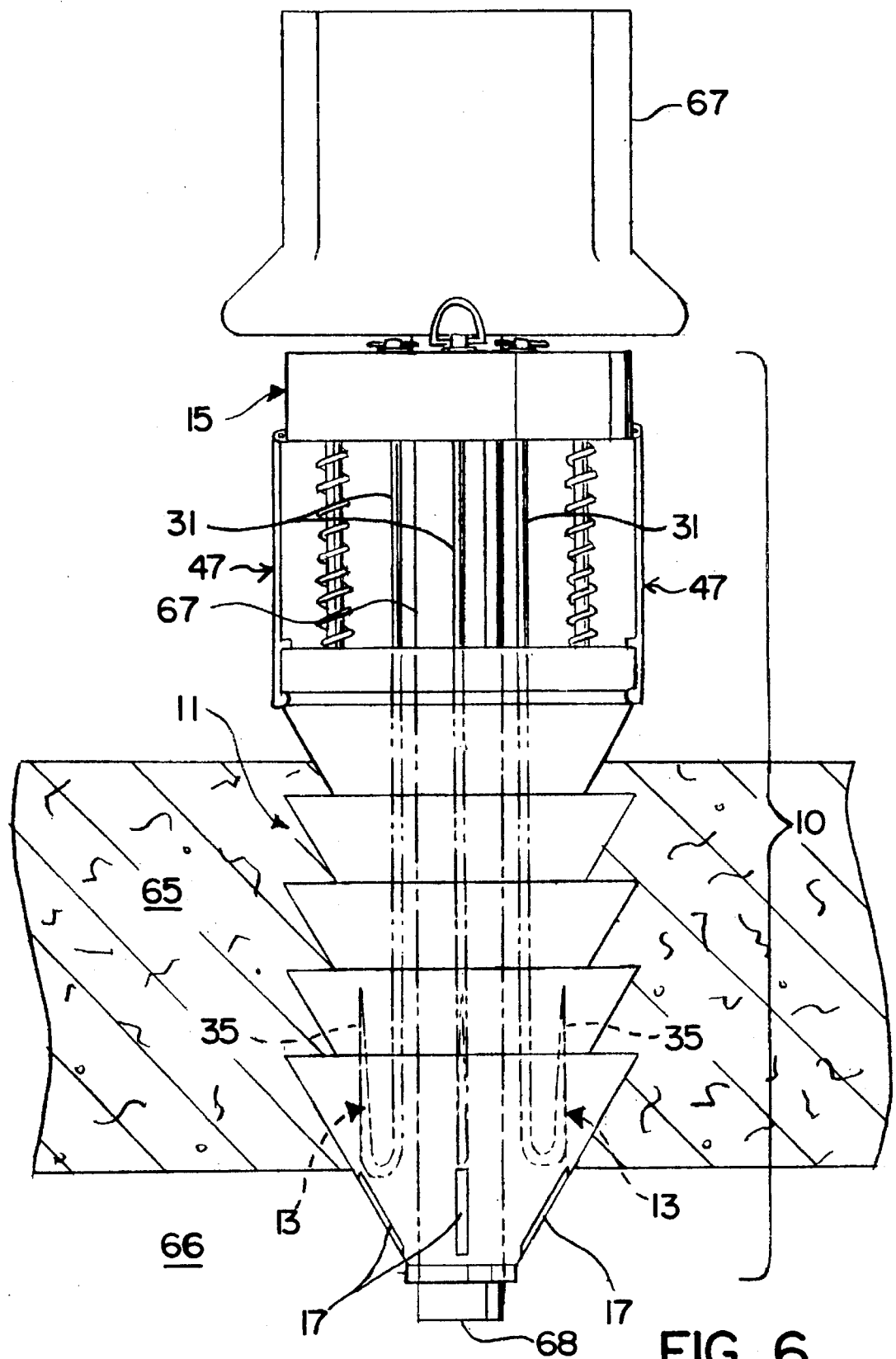
FIG. 6 is a side view, partly in section, of the apparatus of FIG. 1 within a puncture site for stabilizing a portal sleeve prior to puncture site closure.

Use of the apparatus 10 of the present invention for puncture site closure is illustrated in FIGS. 6–14, wherein the stabilizer 11 is guided into a puncture site created in the wall 65 of an anatomical cavity 66 with a trocar or some other penetrating member (not shown), over a portal sleeve 67 after a distal end 68 of the sleeve 67 has been positioned within the anatomical cavity 66 as shown in FIG. 6. Once positioned within the wall 65 of the cavity 66, the natural resiliency of the surrounding tissue of the cavity wall 65 engages the external tissue engaging surface 21 of the stabilizer 11 to stabilize the portal sleeve 67.

Figure 7:
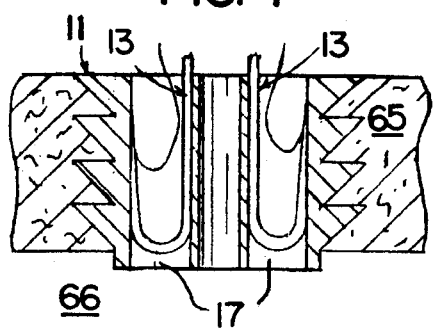
Figure 8:
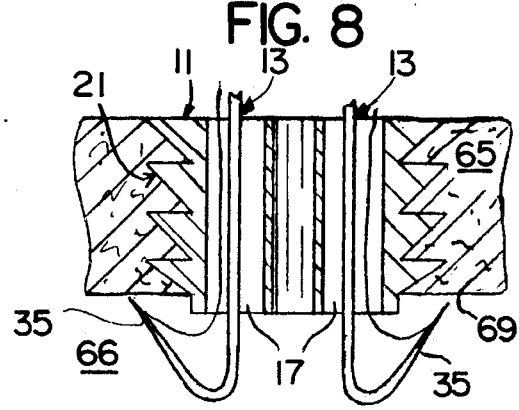
Figure 9:
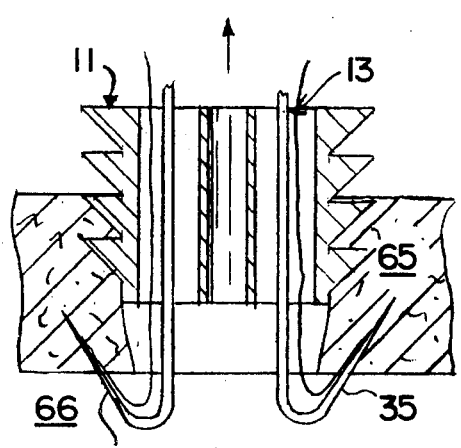
Figure 10:
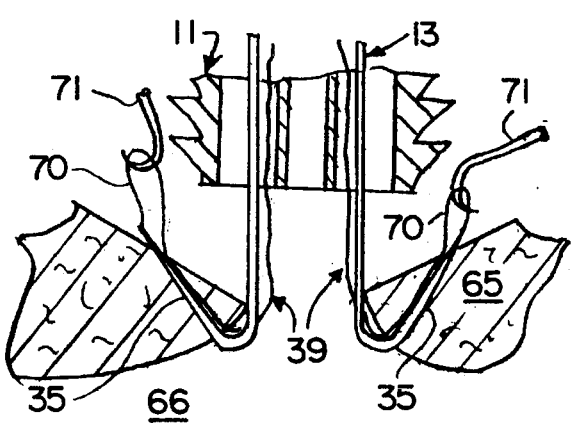
Figure 13:
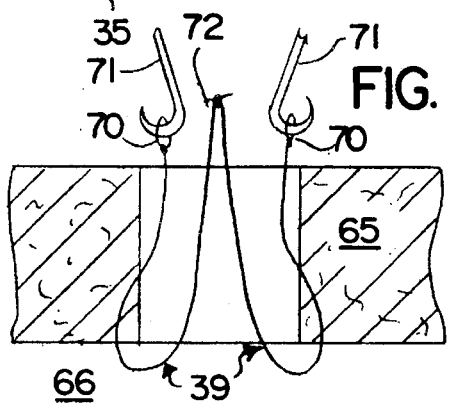
Figure 14:
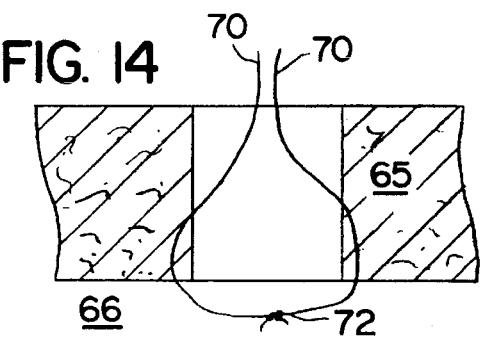
Figure 15:
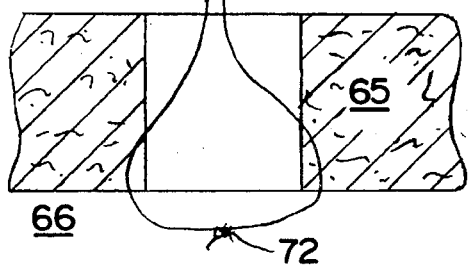
Figure 16:
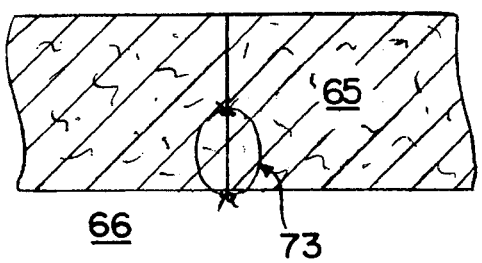

The sharp tissue penetrating tips 35 of the hooks 13 are maintained within the passages 17 during insertion of the stabilizer 11 into the puncture site as well as during procedures performed through the portal sleeve 67. Unintentional deployment and exposure of the sharp tissue penetrating tips 35 is avoided by securing the proximal ends of the legs 31 of each hook 13 to the hub 15 and locking the hub 15 a predetermined distance from the stabilizer 11 with the hinged latching arms 47. After the procedure has been performed, the portal sleeve 67 can be left in place, or removed as shown in FIG. 7, prior to closing the puncture site. To close the puncture site, the hooks 13 are displaced from their retracted positions within the passages 17 into deployed positions with the sharp tissue penetrating tips 35 exposed as shown in FIG. 8, by distal displacement of the hub 15 toward the proximal end 27 of the stabilizer 11. The resulting distal movement of the hooks 13 causes the sharp tissue penetrating tips 35 of the hooks 13 to protrude out of respective open distal ends of the passages 17, and as a consequence of being biased radially outward, to spring into a position whereby the sharp tissue penetrating tips 35 of the hooks 13 face proximally toward a distal surface 69 of the cavity wall 65 at locations spaced radially outward of the exterior tissue engaging surface 21 of the stabilizer 11. With the sharp tissue penetrating tips 35 of the hooks 13 exposed, the puncture site closure apparatus 10 is retracted to cause the tips 35 to penetrate the tissue of the cavity wall 65 surrounding the puncture site as shown in FIG. 9. Continued retraction of the puncture site closure apparatus 10 in a proximal direction away from cavity wall 65 causes the puncture site to invert as shown in FIG. 10 and the sharp tissue penetrating tips 35 of the hooks 13 to pierce through the cavity wall 65 to protrude externally of the wall 65. The distal end 70 of each length of suture material 39 carried by a tissue penetrating tip 35 is then grasped with an implement 71, such as a hook or forceps, or by hand, and detached from the sharp tissue penetrating tip 35 of each hook 13. The puncture site closure apparatus 10 is then advanced distally back into the puncture site as shown in FIG. 11 until the sharp tissue penetrating tips 35 of the hooks 13 no longer penetrate into the cavity wall. The legs 31 of the hooks 13 are all rotated in the same direction using knobs 32 to fold the sharp tissue penetrating tips 35 inward against the distal end 25 of the stabilizer 11 so that the puncture site closure apparatus 10 can be removed from the puncture site without snagging the surrounding tissue, leaving only the lengths of suture material 39 threaded through the cavity wall as shown in FIG. 13. The formerly proximal ends 72 of the lengths of suture material 39 are then cut away from the spools 45, the puncture site closure apparatus 10 removed from the site and the ends 72 knotted together while the formerly distal grasped ends 70 are held separately outside the cavity wall. The grasped ends 70 of the suture material 39 are then pulled away from the cavity wall to bury the knotted ends 72 as shown in FIG. 14 and a slip knot or other medically-acceptable knotting technique is used to join the grasped ends 70 of the suture material 39 outside of the puncture site as shown in Fig. 15, so that when the knot is slid into the opening a suture loop 73 is formed as shown in FIG. 16, and the tension of the suture adjusted to the close the puncture site.

Figure 17:
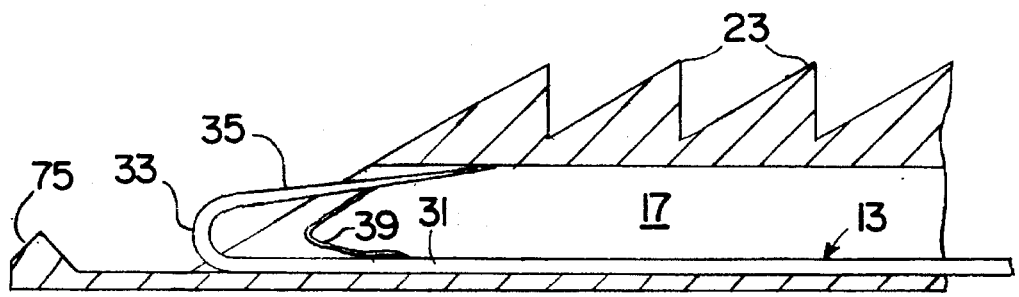
FIG. 17 is a broken view of the distal end of a modified stabilizer for use as a housing in the apparatus of the present invention.
Figure 18:
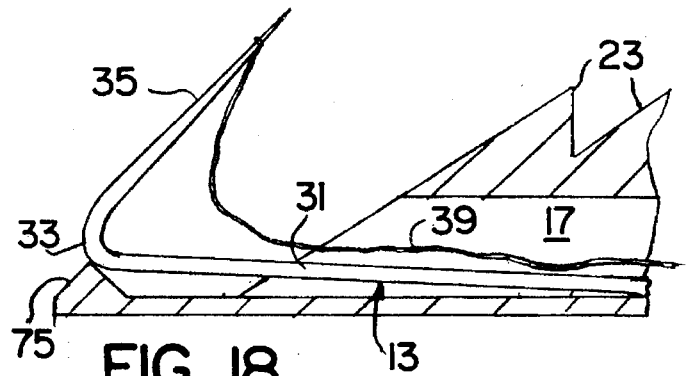
FIG. 18 is a broken view of the modified stabilizer of FIG. 17 with a hook deployed.

A modification of the puncture site closure apparatus 10 is illustrated in FIGS. 17 and 18, wherein a ramp or annular protrusion 75 is formed at the distal end 25 of the stabilizer 11 to cam the distal end of each hook 13 radially outward as the hooks 13 are displaced distally from the retracted positions within the passages 17 to their deployed positions wherein their sharp tissue penetrating tips 35 protrude from the open distal ends of the passages 17. The ramp 75 is spaced distally from the open distal end of each passage 17 so as to allow unencumbered displacement of the hooks 13 until the sharp tissue penetrating tip 35 of each hook 13 is ready to emerge. Thus, a longitudinal distance between the open distal end of passage 17 and the ramp 75 approximately equals the length of the tissue penetrating tip 35 (i.e., the throat dimension of each hook).

Figure 21:
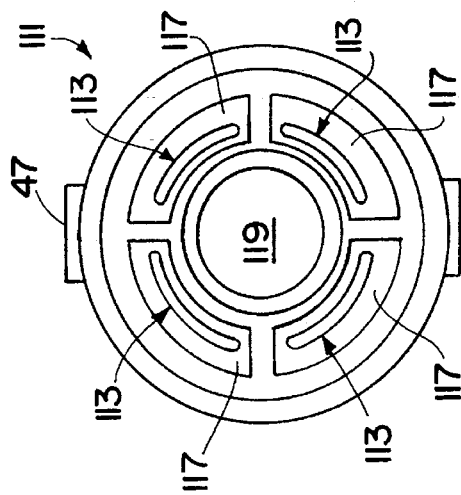
FIG. 21 is an enlarged perspective view of a hook for use with the apparatus of FIG. 19.
Figure 19:
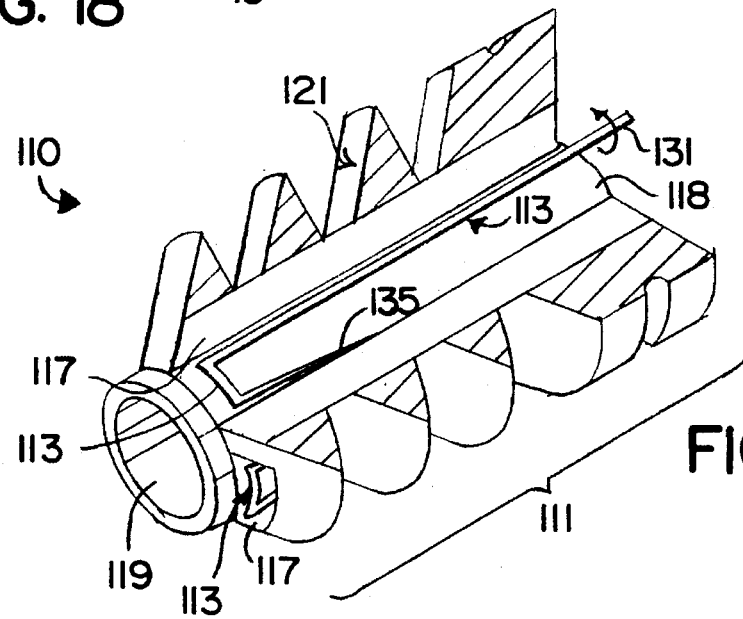
FIG. 19 is a perspective view of another modification of the apparatus according to the present invention.
Figure 22:
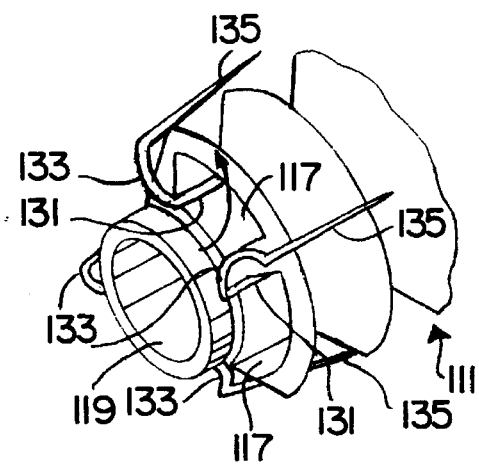
FIG. 22 is a broken perspective view of the apparatus of Fig. 19 with hooks deployed.

Another modification of the puncture site closure apparatus 10 is illustrated in FIGS. 19–22, wherein the modified puncture site closure apparatus 110 includes a stabilizer 111 having angularly spaced elongate passages 117 with arcuate cross-sections extending longitudinally from proximal to distal ends of the stabilizer 111 in the region between the central lumen 119 and the tissue engaging surface 121, and hooks 113 configured to conform to the arcuate cross-section of the passages 117. As best seen in FIG. 20, each hook 113 includes an elongate leg 131, a generally coplanar tissue penetrating tip 135 and an out of plane radius or elbow 133 joining the leg 131 and tip 135 and configured to conform to the arcuate inner wall 118 of each passage 117. Each hook 113 is thus able to fold essentially flush against the arcuate inner wall 118 of each passage 117 when in a retracted position within the stabilizer 111 as shown in FIGS. 19 and 21. The gap width (G in FIG. 20) of each conformal hook 113 is the distance between the leg 131 and the tissue penetrating tip 135, and is chosen according to the chord length of the arcuate inner wall 118 of each passage 117. For this reason, if only two conformal hooks 113 are employed, for example, each hook will circumscribe almost half the circumference of the lumen 119 and thus have a gap width approximating the diameter of the lumen 119. Similarly, for three conformal hooks 113, the gap width of each hook 113 will be greater than or equal to the radius of the lumen 119.

Only the distal portions of the puncture site closure apparatus 110 have been illustrated in FIGS. 19–22; however, it will be appreciated that the proximal portions can be formed with any cooperating structure to distally advance and rotate the hooks 113, such as that shown in FIG. 1. Accordingly, operation of the puncture site apparatus 110 will be described with reference to the elements of the proximal portion shown in FIG. 1.

In use, a hub carrying the hooks 113 is displaced from a locked position relative to the stabilizer 111 to a position such as that shown in FIG. 5 so that the hooks 113 move from their retracted position within the stabilizer 111 to a deployed position wherein the sharp tissue penetrating tip 135 of each hook 113 protrudes from the open distal end of an arcuate passage 117 so as to be exposed. Rotation of the legs 131, for example by turning individual knobs connected to the proximal ends of the legs 131, raises the sharp tissue penetrating tips 135 from their folded position to a radially outward extending position, shown in Fig. 22, wherein a tip 135 of each hook 113 faces proximally toward the exterior tissue engaging surface 121 of the stabilizer 111. The relatively large gap width of the conformal hooks 113 ensures that each tip 135 is spaced radially outward of the tissue engaging surface 121 so that when the stabilizer 111 is inserted within the wall of an anatomical cavity, proximal movement of the elevated hooks 113 will cause the tip 135 of each hook 113 to penetrate the tissue surrounding the stabilizer 111 and the puncture site.

Rotation of conformal hook 113, or any of the other hooks previously described, can be accomplished using any suitable mechanism for individually turning or concurrently turning the legs of each hook. A modification of the puncture site closure apparatus of the present invention for concurrently turning the legs of the hooks is illustrated in FIG. 23, wherein the modified puncture site closure apparatus 210 includes a single knob 211 connected to a rotating shaft 212 which passes through the proximal wall 215 of a cylindrical hub 217 and terminates in a sun gear 219 intermediate the proximal and distal walls 215 and 216 of the hub 217. The sun gear 219 is centrally located between the legs 231 of two or more hooks 213 which can be the same as any of the hooks thus far described. Gear teeth 221 are either formed on sprockets carried by the legs 231 or integrally formed on an exterior surface of each leg 131 adjacent the sun gear 219. The legs 231 are suspended between the proximal and distal walls 215 and 216 of the hub 217 and are held in position relative to the cylindrical hub 217 with flanges 221 formed on the legs 231 proximate the distal wall 216 so that the gear teeth 221 on the legs 231 are engaged with the teeth of the sun gear 219 and rotation of the knob 211 in a first direction will cause rotation of each leg 231 in a second, opposite direction, thereby folding or unfolding the hooks 213. Mechanical detents can be provided to lock the gears and thus the hooks 213 in one or more positions. Additionally, ring handles such as those shown in FIG. 1 can be substituted for the knob 211 shown in FIG. 23, and can be pivotably connected to a proximally protruding portion of the rotating shaft 212 and thereby rotatable into a position flush with the proximal wall 215 of the cylindrical hub 217.

Also in FIG. 23, an arrangement for a spool 223 is shown in which the spool 223 is mounted on a spindle 225 that is essentially parallel to a longitudinal axis of the cylindrical hub 217 and stabilizer. The spool 223 is advantageously disposed within a cylindrical spool housing 229 formed in the proximal wall 215 of the hub 217 to allow replacement spools to be fitted. A feed hole 232 is defined between the spool housing 229 and the distal wall 216 of the hub 217 to allow passage of lengths of suture material 239 from the spool 223 to the tip of each hook 213 carried by the hub 17.

Another modification of the puncture site closure apparatus of the present invention is illustrated in FIGS. 24–26, wherein the modified puncture site closure apparatus 310 includes at least two outwardly turned hooks 311; four being shown and each having a hollow leg 313 with an acutely bent distal portion 315 terminating in a sharp tissue penetrating tip 317. The sharp tissue penetrating tip 317 of each hook 311 is normally angled back toward the proximal end 319 of the leg 313 at a diverging angle to define a tissue receiving space 321 of diminishing width in a distal direction. At least the bent distal portion 315 of each hook 311 is formed of a resilient or semi-rigid medically-acceptable material so as to be deformable to fit within a cannula or other portal sleeve and can be bioabsorbable or non-bioabsorbable. As best seen in FIG. 26, lengths of suture material 325 run through one or more of the hollow legs 313 and exit near openings 327 in the sharp tissue penetrating tips 317 of the legs 313. A continuous slotted opening 323 is formed along the length of each hook 311 and is configured to allow removal of the individual lengths of suture material 325. The legs 313 are bundled together with the slotted openings 323 facing outward using adhesives or any other suitable means of fixation.

Use of the puncture site closure apparatus 310 of FIG. 24 is illustrated in FIGS. 27–33, wherein only those steps preceding knotting of the threaded lengths of suture material 325 are shown; it being understood that the knotting method previously described with reference to FIGS. 13–16 can also be used in connection with the lengths of suture material placed using the puncture site closure apparatus 310.

In use, a portal sleeve or cannula 329 is positioned within the wall 331 of an anatomical cavity 333, as shown in FIG. 27, through a puncture site created by means of a penetrating member, such as a trocar, disposed temporarily within the portal sleeve 329 to puncture the cavity wall 331 and subsequently withdrawn leaving the sleeve 329 in place as a housing or portal for passage of medical instruments into the anatomical cavity 333. To close the puncture site, the puncture site closure apparatus 310 is advanced distally through the sleeve 329 with the distal portion 315 of each hook 311 being deformed elastically and resiliently inward by the sleeve 329 and with lengths of suture material 325 carried within each leg 313. The puncture site closure apparatus 310 is advanced distally until the sharp tissue penetrating tips 317 of the hooks 311 emerge from the open distal end 335 of the sleeve 329 and spring radially outward as shown in FIG. 28 to face the distal surface 337 of the cavity wall 331.

Referring now to FIG. 29, the entire puncture site closure apparatus 310 is retracted proximally to cause the proximally-facing sharp tissue penetrating tips 317 of the legs 313 to penetrate into the tissue of the cavity wall 331 surrounding the puncture site. The apparatus 310 is retracted proximally until the tissue surrounding the puncture site is drawn up and inverted as shown in FIG. 30 so that the sharp tissue penetrating tips 317 protrude from the tissue surrounding the puncture site and the lengths of suture material 325 can be advanced through the openings 327 in the sharp penetrating tips 317 and grasped using forceps 341 or the like. With the free ends 339 held outside the cavity wall 331, the sleeve 329 and hooks 311 are advanced distally through the puncture site once more, the lengths of suture material 325 drawing out of the slotted openings (elements 323 in FIG. 26) when pulled laterally outward as shown in FIG. 31. The distal end 335 of the sleeve 329 is distally spaced a predetermined distance from the distal surface 337 of the cavity wall 331 and held in place while the hooks 311 are withdrawn proximally, the distal portion 315 of each hook 311 straightening out as it is drawn within the sleeve 329 as shown in FIG. 32. The puncture site closure apparatus 310 and sleeve 329 are then completely withdrawn, leaving a plurality of lengths of suture material 325 threaded through the inner distal layers of the cavity wall 331 at two or more locations around the puncture site to form suture loops using standard knotting techniques to close the puncture site.

From the above, it will be appreciated that the apparatus of the present invention can be used to quickly and effectively close a puncture site opening formed by a penetrating member such as a trocar as well as to perform procedures such as anastomosis, reconstructive surgery, such as bladder reattachment or to repair a hernia or ruptured bowel or to suture any other opening in anatomical tissue or separating tissue segments. Hence, by "close" or "repair" is meant to approximate or suture together any congenital or non-congenital gaps between tissue segments such as adjacent tubular vessels or disconnected organs and holes or recesses in anatomical tissue such as bowel ruptures, hernias or puncture site openings in a cavity wall. It will also be appreciated that the apparatus of the present invention can be inserted into an anatomical cavity through various housings including cannulas or portal sleeves and plugs or other structures used for stabilizing cannulas or portal sleeves.

The puncture site closure apparatus of the present invention can have two or more hooks that are acutely bent, curved or configured in any way to penetrate tissue proximate a puncture site or other opening in anatomical tissue. The hooks can be solid, hollow or slotted to pass lengths of suture material through inner layers of the cavity wall; and when hollow, can also be used to precisely administer medicaments to the tissue at the puncture site. Lengths of suture material need not be carried by all hooks at all times, and in certain procedures it may be desirable to have less than the full number of hooks provided carrying lengths of suture material. Further, while a stabilizer having frustoconical ridges has been described, any housing including portal sleeves or cannulas or any structure carried on a portal sleeve or cannula can be used, including stabilizers having exterior tissue engaging surfaces that are threaded or unthreaded, conical, saddle shaped or with other configurations suitable for stabilizing a sleeve. A spring can be held in compression between telescoping tubular members for use as guide pins between the hub and stabilizer of the puncture site closure apparatus, and when telescoping members are used it may not be necessary to form recesses on one or both opposing surfaces of the hub and stabilizer. The guide pins of the present invention can also be provided with locking detents to position the hub at one or more predetermined positions relative to the stabilizer, thereby obviating the need for separate latching arms.

When the puncture site closure apparatus of the present invention is configured for use through a portal sleeve or cannula, the two or more hooks employed can be configured as having separate legs which are joined lengthwise or as having a single leg from which multiple tissue penetrating tips emerge. Further, it will be appreciated that the proximal end of the puncture site closure apparatus shown in FIG. 24 can be configured to cooperate with any handle structure suitable for manipulating the apparatus through a portal sleeve and engaging the anatomical tissue adjacent an opening.

In as much as the present invention is subject to many modifications, variations and changes in detail, it is intended that all subject matter discussed above and shown in the drawings be interpreted as illustrative only and not be taken in a limiting sense.

What is claimed is:

1. An apparatus for suturing together anatomical tissue adjacent an opening comprising at least one length of suture material;

a plurality of hooks having sharp tissue penetrating tips for passing said at least one length of suture material through the anatomical tissue adjacent the opening;

a housing adapted to fit in the opening to define a portal through the anatomical tissue for passage of said hooks; and operating means coupled with said hooks for advancing said hooks from a retracted position within said housing to a deployed position where said tips extend radially outward of said housing to permit said hooks to be retracted proximally relative to the anatomical tissue adjacent the opening to pass said at least one length of suture material through the anatomical tissue when said hooks are in said deployed position and for repositioning said hooks for withdrawal from the opening with said penetrating tips after said at least one length of suture material has been passed through the anatomical tissue.

2. An apparatus for suturing together anatomical tissue adjacent an opening as recited in claim 1 wherein said operating means includes a first mechanism to advance said hooks from said retracted position to said deployed position and a second mechanism to reposition said hooks for withdrawal from the opening.

3. An apparatus for suturing together anatomical tissue adjacent an opening comprising at least one length of suture material;

a plurality of hooks having sharp tissue penetrating tips for passing said at least one length of suture material through the anatomical tissue adjacent the opening; and operating means coupled with said hooks for advancing and retracting said hooks relative to the opening;

wherein said plurality of hooks includes a plurality of legs each having a turned distal portion and further comprising a plurality of lengths of suture material to be passed by said hooks through the anatomical tissue adjacent the opening.

4. An apparatus as recited in claim 3 and further comprising a housing defining a portal through the opening for passage of said hooks.

5. An apparatus as recited in claim 4 wherein said operating means includes a hub positioned proximally of said housing and said legs are carried by said hub.

6. An apparatus as recited in claim 5 and further comprising a spool of suture material carried by said hub to supply said lengths of suture material.

7. An apparatus as recited in claim 5 wherein said housing is a stabilizer with passages formed between proximal and distal ends thereof around a central lumen and said legs extend distally from said hub into said passages.

8. An apparatus as recited in claim 7 wherein said hub is movable between a first position relative to said stabilizer wherein said sharp tissue penetrating tips are held within said passages and a second position wherein said sharp tissue penetrating tips protrude from distal ends of said passages.

9. An apparatus as recited in claim 8 and further comprising a guide pin extending between a proximal face of said stabilizer and a distal face of said hub.

10. An apparatus as recited in claim 8 and further comprising a latching arm hinged to one of said hub and stabilizer and configured to releasably hold said hub a predetermined distance from said stabilizer.

11. An apparatus for suturing together anatomical tissue adjacent an opening comprising at least one length of suture material;

a plurality of hooks having sharp tissue penetrating tips for passing said at least one length of suture material through the anatomical tissue adjacent the opening; and operating means coupled with said hooks for advancing and retracting said hooks relative to the opening;

wherein said plurality of hooks includes a plurality of legs each having a turned distal portion and further comprising a plurality of lengths of suture material and a housing defining a portal through the opening for passage of said hooks, wherein said operating means includes a hub positioned proximally of said housing and said legs are carried by said hub and wherein said housing is a stabilizer with passages formed between proximal and distal ends thereof around a central lumen and said legs extend distally from said hub into said passages, said hub being movable between a first position relative to said stabilizer wherein said sharp tissue penetrating tips are held within said passages and a second position wherein said sharp tissue penetrating tips protrude from distal ends of said passages, and wherein proximal portions of said legs are rotatably held by said hub and further comprising means coupled with said proximal portions for rotating said legs.

12. An apparatus as recited in claim 11 wherein at least said distal portions of said legs are flexible and said passages are smaller than a gap width of said hooks.

13. An apparatus as recited in claim 11 wherein said passages are arcuate in cross section and said hooks are configured to conform to the curvature of said arcuate passages.

14. An apparatus as recited in claim 11 wherein said means for rotating said legs includes gear teeth carried by said legs and a sun gear engaged with said teeth and carried by a rotating shaft that extends through a proximal face of said hub and is connected to a knob.

15. An apparatus for suturing together anatomical tissue adjacent an opening comprising at least one length of suture material;

a plurality of hooks having sharp tissue penetrating tips for passing said at least one length of suture material through the anatomical tissue adjacent the opening; and operating means coupled with said hooks for advancing and retracting said hooks relative to the opening, wherein said plurality of hooks includes a plurality of legs each having a turned distal portion and further comprising a plurality of lengths of suture material, wherein said legs are secured along their length to one another and said operating means includes a manually graspable portion of said secured legs.

16. An apparatus as recited in claim 15 and further comprising a housing defining a portal through the opening for passage of said hooks.

17. An apparatus as recited in claim 16 wherein said housing is a tubular sleeve.

18. An apparatus as recited in claim 17 wherein at least said turned distal portions are flexible and a distance between said sharp tissue penetrating tips of said hooks is greater than an inner diameter of said tubular sleeve.

19. An apparatus for suturing together anatomical tissue adjacent an opening comprising at least one length of suture material;

a plurality of hooks having sharp tissue penetrating tips for passing said at least one length of suture material through the anatomical tissue adjacent the opening; and operating means coupled with said hooks for advancing and retracting said hooks relative to the opening, wherein said plurality of hooks includes a plurality of legs each having a turned distal portion and further comprising a plurality of lengths of suture material, wherein said legs are hollow and open at proximal and distal ends to allow passage of said lengths of suture material through said legs.

20. An apparatus as recited in claim 19 wherein continuous slots are formed in said hollow legs extending from proximal to distal ends thereof.

21. An apparatus for suturing together anatomical tissue adjacent an opening comprising at least one length of suture material;

a plurality of hooks having sharp tissue penetrating tips for passing said at least one length of suture material through the anatomical tissue adjacent the opening; and operating means coupled with said hooks for advancing and retracting said hooks relative to the opening, wherein said plurality of hooks includes a plurality of legs each having a turned distal portion and further comprising a plurality of lengths of suture material, wherein distal ends of said lengths of suture material are attached near the sharp tissue penetrating tips of said hooks.

22. A method of suturing together anatomical tissue adjacent an opening comprising the steps of penetrating the anatomical tissue adjacent the opening with sharp proximal-facing tips of at least two outwardly turned hooks;

pulling said outwardly turned hooks in a proximal direction to invert the tissue adjacent the opening;

piercing through the inverted tissue to expose the proximal facing tips;

using the hooks to pass lengths of suture material through the anatomical tissue;

grasping distal ends of said lengths of suture material; and drawing the adjacent anatomical tissue together.

23. A method of suturing together anatomical tissue adjacent an opening as recited in claim 22 wherein said drawing step includes drawing the adjacent tissue together via the lengths of suture material to close the opening in the anatomical tissue.

24. A method of suturing together anatomical tissue adjacent an opening as recited in claim 23 wherein said hooks are hollow and further comprising, prior to said grasping step, advancing said lengths of suture material through the hooks.

25. A method of suturing together anatomical tissue adjacent an opening as recited in claim 23 and further comprising, prior to said grasping step, attaching said lengths of suture material adjacent distal ends of the tissue penetrating tips and pulling said lengths through the tissue with the hooks.

26. A method of suturing together anatomical tissue adjacent an opening as recited in claim 23 and further comprising, after said grasping step and prior to said drawing step, withdrawing said sharp tissue penetrating tips from the tissue.

27. A method of suturing together anatomical tissue adjacent an opening as recited in claim 26 and further comprising, prior to said penetrating step, passing said hooks through a housing disposed within the opening and, after said withdrawing step, rotating said hooks into said housing and removing said hooks and housing from the opening.

28. A method of suturing together anatomical tissue adjacent an opening as recited in claim 27 wherein the step of passing hooks through a housing includes the step of bending said hooks resiliently inward.

29. A method of suturing together anatomical tissue adjacent an opening as recited in claim 27 and further comprising, after said passing step, rotating said sharp tissue penetrating tips of said hooks outward of the housing to face tissue adjacent the opening.

\* \* \* \* \*